US00PP25904P2

(12) United States Plant Patent
Smith

(10) Patent No.: US PP25,904 P2
(45) Date of Patent: Sep. 15, 2015

(54) ***CHRYSANTHEMUM* PLANT NAMED 'CIFZ0026'**

(50) Latin Name: *Chrysanthemum×morifolium*
Varietal Denomination: CIFZ0026

(71) Applicant: SYNGENTA PARTICIPATIONS AG, Basel (CH)

(72) Inventor: Mark A. Smith, Alva, FL (US)

(73) Assignee: Syngenta Participations AG, Basel (CH)

( * ) Notice: Subject to any disclaimer, the term of this patent is extended or adjusted under 35 U.S.C. 154(b) by 40 days.

(21) Appl. No.: 13/999,342

(22) Filed: Feb. 12, 2014

(51) Int. Cl.
*A01H 5/02* (2006.01)

(52) U.S. Cl.
USPC ..... Plt./290

(58) Field of Classification Search
USPC ..... Plt./290, 289, 287
CPC ..... A01H 5/0255; A01H 5/025; A01H 5/02
See application file for complete search history.

*Primary Examiner* — Kent L Bell
(74) *Attorney, Agent, or Firm* — Joshua L. Price

(57) ABSTRACT

A new *Chrysanthemum* plant named 'CIFZ0026' particularly distinguished by the large, orange-bronze, decorative-type flowers, medium to large plant size with round mound habit, and an early October natural flowering response.

1 Drawing Sheet

Latin name of the genus and species of the plant claimed: *Chrysanthemum×morifolium.*

Varietal denomination: 'CIFZ0026'.

BACKGROUND OF THE NEW PLANT

The present invention comprises a new *Chrysanthemum*, botanically known as *Chrysanthemum×morifolium*, and hereinafter referred to by the variety name 'CIFZ0026'.

'CIFZ0026' is a product of a planned breeding program. The new cultivar has large, orange-bronze, decorative-type flowers, medium to large plant size with round mound habit, and a natural season flowering response in early October.

'CIFZ0026' originated from a hybridization made in August 2008 in a greenhouse in Tenjo, Columbia. The female parent was the unpatented, proprietary plant designated '06-M131', with bronzy yellow, decorative-type flower that fades more rapidly, and although the natural season response is similar, the blackcloth response is almost a week faster when compared to 'CIFZ0026'.

The male parent of 'CIFZ0026' was the unpatented, proprietary plant designated as '04-M277' with smaller, purple inflorescence with more disc florets, smaller overall plant with more upright habit, and flowers two weeks faster in the natural season when compared to 'CIFZ0026'.

The resultant seed was sown in June 2009 and grown outdoors in Alva, Fla., USA.

'CIFZ0026' was selected as one flowering plant within the progeny of the stated cross on Nov. 9, 2009 in Alva, Fla.

The first act of asexual reproduction of 'CIFZ0026' was accomplished when vegetative cuttings were propagated from the initial selection in January 2010 in a greenhouse in Alva, Fla.

BRIEF SUMMARY OF INVENTION

Horticultural examination of plants grown from cuttings of the plant initiated in January 2010, and continuing thereafter, has demonstrated that the combination of characteristics as herein disclosed for 'CIFZ0026' are firmly fixed and are retained through successive generations of asexual reproduction.

'CIFZ0026' has not been observed under all possible environmental conditions. The phenotype may vary significantly with variations in environment such as temperature, light intensity, and day length.

A Plant Breeder's Right for this cultivar was applied for in Canada on Mar. 8, 2013, No. 13-7960. 'CIFZ0026' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ0026' with colors being as true as possible with an illustration of this type.

Figure 1:
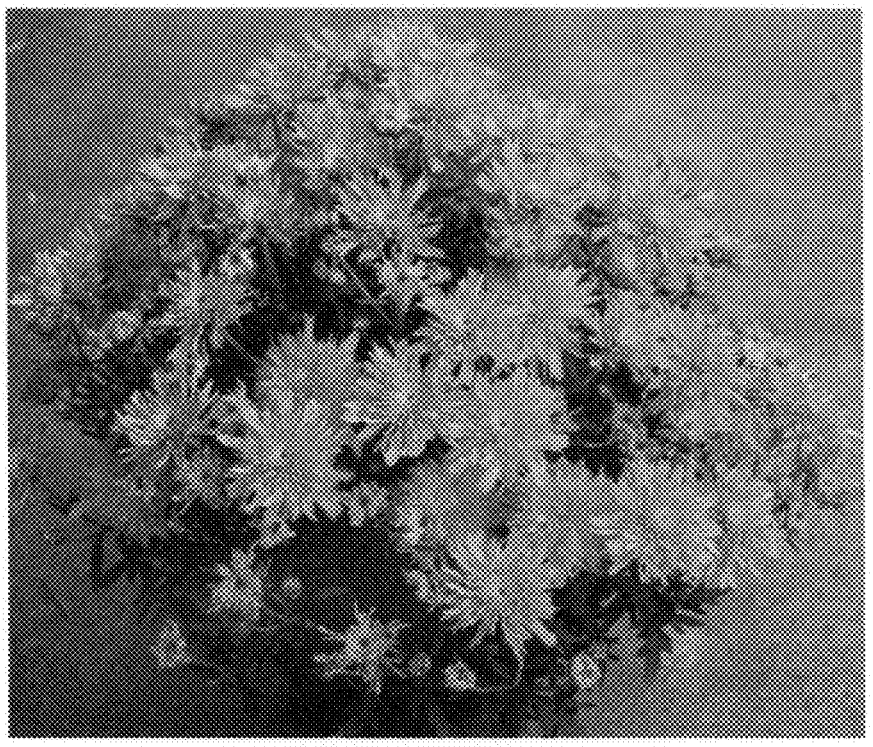
Figure 2:
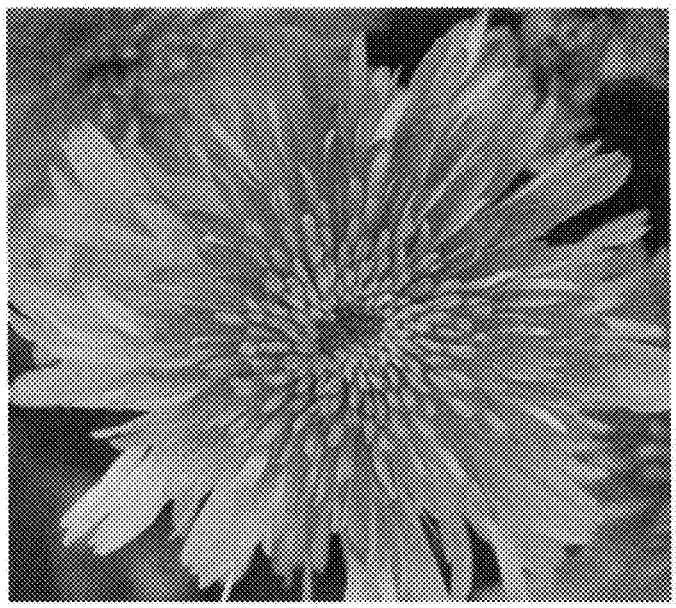

The photographic drawings show in FIG. 1 a flowering potted plant of the new variety, and in FIG. 2 is a close-up of an inflorescence.

DETAILED BOTANICAL DESCRIPTION

The plant descriptions, measurements, and aforementioned photographs were taken in Gilroy, Calif. in late August 2013 outdoors in natural light. These plants had been grown one (1) plant in a 6 inch pot in a greenhouse trial in Gilroy, Calif. Blackout by black cloth was applied to control day length and to induce early flowering. The plants used were about 10-11 weeks old and were not pinched.

The aforementioned photographs were taken in Gilroy, Calif. in August of 2013 outdoors. These plants were approximately 10-11 weeks of age and were not pinched.

Color references are made to The Royal Horticultural Society Colour Chart (R.H.S.) 2001.

TABLE 1

DIFFERENCES BETWEEN THE NEW VARIETY 'CIFZ0026' AND TWO MOST SIMILAR VARIETIES

| | 'CIFZ0026' | 'Yoashley' (U.S. Plant Pat. No. 18,916) |
|---|---|---|
| Inflorescence: | Larger, with more disc florets | Smaller, with fewer disc florets |
| Infloresence, color: | Lighter hue of orange | Deeper/darker orange |
| Plant habit, overall size: | Larger, mainly wider | Smaller, narrower |

| | 'CIFZ0026' | 'Spicy Yocheryl' (U.S. Plant Pat. No. 13,221) |
|---|---|---|
| Flower color: | Brighter shade of orange, and uniform | Two-tone color |
| Flower shape: | Similar size, but with more disc florets | Less disc florets |
| Plant habit: | Somewhat rounder<br>Somewhat wider | Slightly more upright<br>Slightly narrower |

Plant:

*Form, growth and habit.*—Herbaceous garden-type, stems upright and outwardly spreading, freely branching, strong and moderately vigorous growth habit.

*Plant height.*—18-20 cm.

*Plant height (inflorescence included).*—20-26 cm.

*Plant width.*—37-40 cm.

Roots:

*Number of days to initiate roots.*—About 4 days at about 22 degrees C.

*Number of days to produce a rooted cutting.*—4-6 days at 22 degrees C.

*Type.*—Fine, fibrous, free branching.

*Color.*—RHS N155B but whiter.

Foliage:

*Arrangement.*—Alternate.

*Immature leaf, color upper surface.*—RHS 137A, but appears lighter due to the surface being densely covered by pubescence.

*Immature leaf, color lower surface.*—RHS 137C.

*Mature leaf, color upper surface.*—RHS 137A.

*Mature leaf, color lower surface.*—RHS 137C.

*Length.*—5.3-5.8 cm.

*Width.*—2.7-3.4 cm.

*Shape.*—Ovate, relatively long.

*Base shape.*—Attenuate.

*Apex shape.*—Apiculate.

*Margin.*—3 distinct lobes, irregular serrulate.

*Texture, upper surface.*—Slight pubescence, bifid hair.

*Texture, lower surface.*—Heavily covered by bifid hair.

*Color of veins, upper surface.*—RHS 144B.

*Color of veins, lower surface.*—RHS 144C.

*Pattern of veining.*—Palmate.

*Petiole color.*—RHS 144B.

*Length.*—0.8-1.3 cm.

*Diameter.*—0.25-0.30 cm.

*Texture.*—Bifid hair.

Stem:

*Quantity of main branches per plant.*—8-10.

*Color of stem.*—RHS 137C.

*Length of stem.*—12-15 cm.

*Diameter.*—0.4 cm.

*Length of internodes.*—0.5-1.0 cm.

*Texture.*—Heavily hairy, bifid hairs.

*Color of peduncle.*—RHS 137C.

*Length of peduncle.*—5.5-7.5 cm.

*Peduncle diameter.*—0.2 cm.

*Texture.*—Bifid hairs.

Inflorescence:

*Type.*—Compositae, solitary, decorative-type with the inflorescences borne terminally above foliage, ray florets arranged acropetally on a capitulum.

*Quantity of short days to flowering (response time).*—Approximately 7 weeks.

*Natural season flowering.*—Early October.

*Quantity of inflorescences per plant.*—About 50, plus many additional buds.

*Lastingness of individual blooms on the plant.*—About 6 weeks from first color.

*Fragrance.*—Slightly spicy.

Bud (just when opening/showing color):

*Color.*—RHS 4B.

*Length.*—0.6-0.8 cm.

*Width.*—1.3-1.5 cm.

*Shape.*—Oblate.

Immature infloresence:

*Diameter.*—4-5 cm.

*Color of ray florets, upper surface.*—RHS 4B, apex RHS 172C (slight).

*Color of ray florets, lower surface.*—Mainly RHS 4B with shades of 34B.

Mature infloresence:

*Diameter.*—6.1-6.5 cm.

*Depth.*—1.5 cm.

*Total diameter of disc.*—0.3-0.4 cm.

*Receptacle color.*—RHS 138B.

*Receptacle height.*—0.2 cm.

*Receptacle diameter.*—0.3-0.4 cm.

Ray florets:

*Average quantity of florets.*—160-180 in many whorls.

*Color of florets, upper surface, general tonality.*—Several shades of orange and greyed-orange, with the outer whorls of florets displaying lighter shades than the inner ones.

*Outmost rays.*—RHS 9C overlaid with shades of RHS 26C.

*Rays of the inner whorls.*—RHS N172C to shades of RHS 26A of N163D.

*Color of florets, lower surface.*—RHS 12B with slight shades of RHS 22A.

*Length.*—2.6-2.9 cm.

*Width.*—0.4-0.5 cm.

*Shape.*—Oblong.

*Apex shape.*—Praemorse.

*Base shape.*—Cuneate.

*Margin.*—Entire.

*Texture, upper surface.*—Papillate.

*Texture, lower surface.*—Papillate.

Disc florets:

*Average quantity of florets.*—About 16 to 25.

*Color of florets.*—RHS 1C with 13A apex.

*Length.*—0.25 cm.

*Width.*—0.1 cm.

*Shape.*—Tubular, elongated.

*Apex shape.*—Acute, 5 pointed.

Phyllaries:

*Quantity.*—23-25.

*Color, upper surface.*—RHS 137D.

*Color, lower surface*.—RHS 137A to 137B.
*Length*.—0.6-0.8 cm.
*Width*.—0.1-0.15 cm.
*Shape*.—Linear to lanceolate.
*Apex shape*.—Acute.
*Base*.—Fused.
*Margins*.—Entire.
*Texture, upper surface*.—Glabrous.
*Texture, lower surface*.—Bifid hair.

Reproductive organs:

*Pistil*.—1, developed in both ray and disk florets.
*Length*.—0.3-0.4 cm.
*Style color*.—RHS 1C.
*Style length*.—0.2-0.3 cm.
*Stigma color*.—RHS 1B.
*Stigma shape*.—Bi-lobed.
*Ovary color*.—RHS 145C.
*Ovary length*.—0.15 cm.
*Ovary width*.—0.1 cm.
*Stamens*.—4, found only on the disc florets.
*Color of filaments*.—RHS 1C.
*Length filaments*.—0.2 cm.
*Anther color*.—RHS 16A.
*Anther length*.—0.1 cm.
*Anther shape*.—Oblong.
*Color of pollen*.—RHS 17B.
*Pollen amount*.—Sparse.
*Fertility/seed set*.—Has not been determined to date.

Disease/pest resistance: Has not been determined to date.

What is claimed is:

1. A new and distinct variety of *Chrysanthemum* plant named 'CIFZ0026' substantially as illustrated and described herein.

* * * * *